United States Patent [19]

White

[11] 4,241,187

[45] Dec. 23, 1980

[54] METHOD AND APPARATUS FOR CELL AND TISSUE CULTURE

[75] Inventor: David C. White, Maple Grove, Minn.

[73] Assignee: United States of America, Washington, D.C.

[21] Appl. No.: 24,247

[22] Filed: Mar. 27, 1979

[51] Int. Cl.³ .............................................. C12M 3/00
[52] U.S. Cl. ................................... 435/284; 435/283; 435/285; 210/321.2; 210/321.3
[58] Field of Search ............... 435/283, 284, 285, 286, 435/240, 241; 210/321 A, 321 B, DIG. 23, 22 R; 128/DIG. 3

[56] References Cited

U.S. PATENT DOCUMENTS

| | | | |
|---|---|---|---|
| 2,996,429 | 8/1961 | Toulmin | 435/285 X |
| 3,734,851 | 5/1973 | Matsumura | 210/22 |
| 3,827,565 | 8/1974 | Matsumura | 210/22 R |
| 3,883,393 | 5/1975 | Knazek et al. | 435/284 X |
| 3,941,662 | 3/1976 | Munder et al. | 435/284 |
| 3,993,560 | 11/1976 | Halpern | 435/284 X |

*Primary Examiner*—R. B. Penland

*Attorney, Agent, or Firm*—Holman & Stern

[57] ABSTRACT

A method and apparatus for culturing biological cells and tissues in high density are disclosed, employing perfused blood as the nutrient source. The cells or tissues are separated from the perfused blood by means of a microporous membrane which is maintained in close contact with the cells or tissues, and which is permeable to plasma solutes and to cell products and impermeable to blood cellular components, whereby continuous diffusion of plasma solutes and cell products takes place between the perfused blood and the cells or tissues through the microporous membrane while maintaining the cells or tissues separated from the cellular components of the blood. The blood flow passageway across the surface of the microporous membrane is designed to enable blood perfusion at a sufficiently high linear velocity so as to avoid thrombosis. Continuous blood perfusion through the blood flow passageway is provided by connecting the blood flow passageway into an arterio-venous shunt constructed in a living donor animal.

2 Claims, 3 Drawing Figures

U.S. Patent    Dec. 23, 1980    4,241,187
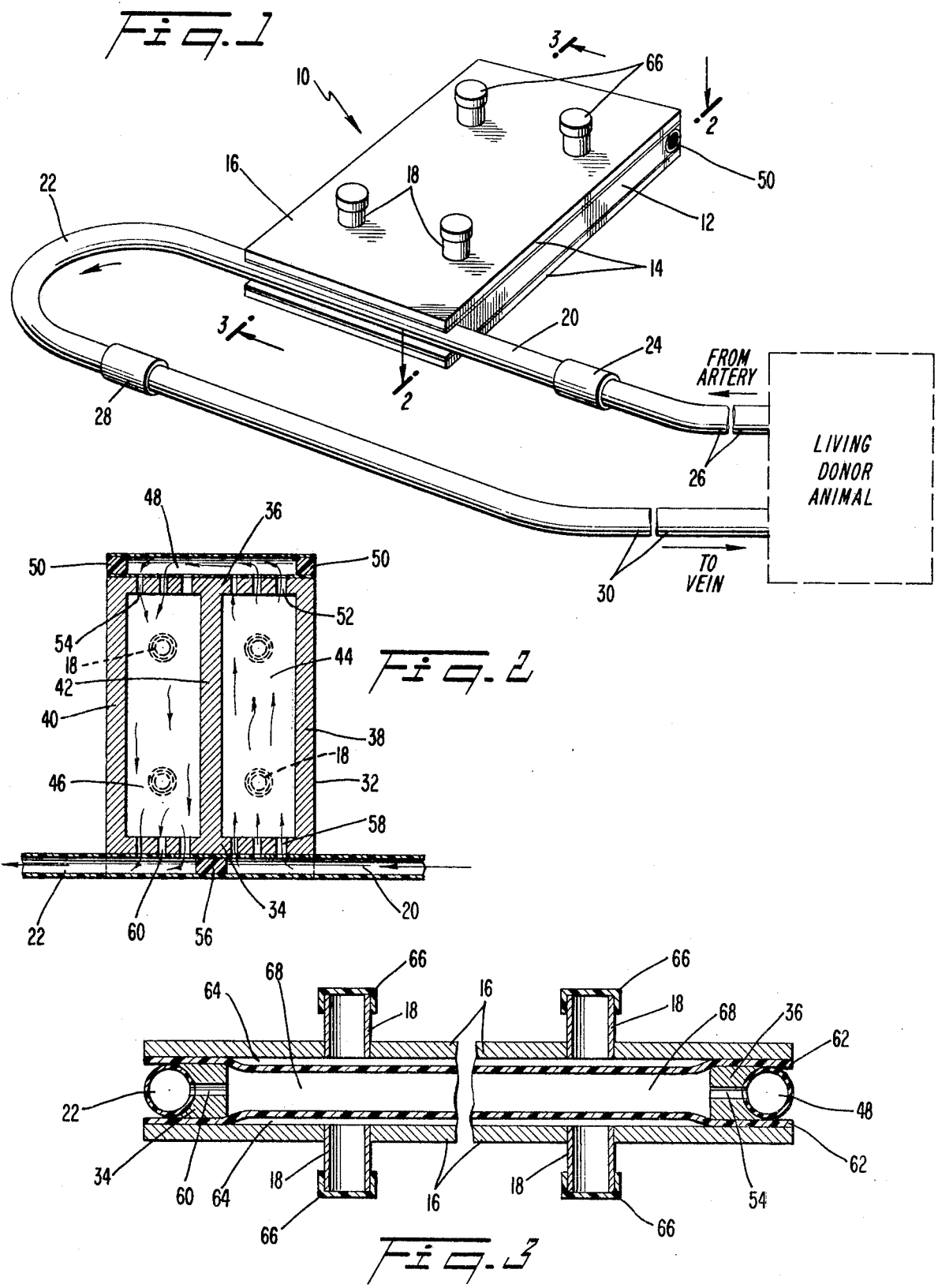

METHOD AND APPARATUS FOR CELL AND TISSUE CULTURE

BACKGROUND OF THE INVENTION

This invention relates to the culturing of biological cells and tissues and, more particularly, to a method and apparatus for cell and tissue culture in high density employing perfused blood as the nutrient source.

Biological cells and tissues cultured in vitro are commonly employed in various biomedical applications, such as, for example, in the development and production of various vaccines, and for the in vitro screening of potential anti-cancer agents prior to in vivo testing in laboratory test animals. The culture systems presently in use typically employ synthetic culture media as the source for the cell nutrients, and for the most part, are incapable of supporting high density cell growth. With such systems, it has been found to be extremely difficult to obtain substantial quantities of cultured cells and tissues which maintain their in vivo function.

Previous studies directed toward the development of more efficient tissue culture systems have led to the findings that cells can be grown in high density in an artificial capillary system where there is a high surface area for diffusion for a given cell volume, and that cells grown in high density maintain their metabolic activity, such as hormone production. It has also previously been found that certain differentiated cell lines, when grown in high density culture, maintain their in vivo function when blood is perfused through the culture system. However, use of perfused blood in tissue culture systems, particularly as the primary culture medium, presents certain problems which must be overcome. First of all, the cells or tissues being cultured must be maintained separated from the cellular components of the perfused blood, since foreign cells coming into contact with immunologically competent host cells tend to be rapidly destroyed by the host cells. Secondly, in the artificial capillary culture systems previously proposed, capillary lumen occlusion from small thrombi and debris in the perfused blood and resultant cell necrosis prevent such systems from remaining patent with respect to perfused blood for periods of time sufficiently long so as to render such systems practical.

SUMMARY OF THE INVENTION

It is, accordingly, a primary object of the present invention to provide a cell and tissue culture system which is capable of supporting high density cell and tissue growth, employs perfused blood as the nutrient source, and is capable of long-term patency with respect to the perfused blood.

Another object of the invention is to provide a cell and tissue culture system in accordance with the preceding object, which permits a sufficiently high linear velocity flow of the perfused blood through the system so as to avoid significant thrombosis.

A further object of the invention is to provide a cell and tissue culture system in accordance with the preceding objects, which permits continuous diffusion of plasma solutes and cell products between the perfused blood and the cells or tissues in culture with minimum molecular diffusion distances and while maintaining the cells or tissues separated from the cellular components of the perfused blood.

Still another object of the invention is to provide a cell and tissue culture system in accordance with the preceding objects, which may be connected into an arterio-venous shunt constructed in a living donor animal to provide continuous blood perfusion through the system.

The above and other objects are achieved in accordance with the present invention by providing a cell and tissue culture apparatus comprising a thin flexible blood-compatible microporous membrane permeable to plasma solutes and to cell products and impermeable to blood cellular components, arranged within a housing means so as to form a culture chamber on one side of the microporous membrane and a blood flow passageway across the membrane surface on the opposite side of the microporous membrane, the culture chamber and the blood flow passageway communicating with each other only through the microporous membrane. The culture chamber is formed between the microporous membrane and a wall of the housing means, with the membrane being superimposed upon the wall and bonded thereto around its periphery, the spacing between the wall and the membrane being such that in its empty condition, the culture chamber is substantially flat. The culture chamber is provided with ports through the wall of the housing means for introduction and retrieval of the cells and tissues. When cells or tissues are introduced into the substantially flat culture chamber, they become wedged against the microporous membrane and are thereby maintained in close contact therewith so as to minimize their molecular diffusion distance from the perfused blood on the opposite side of the membrane. The housing means is further provided with a blood inlet means and a blood outlet means at opposite ends of the blood flow passageway. The blood flow passageway is designed so that the perfused blood will flow therethrough at a linear velocity sufficiently high so as to avoid significant thrombosis, and preferably is formed in a plurality of sections, each of which extends across a separate parallel area of the microporous membrane surface. In its preferred embodiment, the cell and tissue culture apparatus includes a pair of said culture chambers arranged within the housing means in spaced parallel relation to each other between two opposite walls of the housing means and on opposite sides of the blood flow passageway, whereby blood perfused through the passageway simultaneously contacts the surfaces of the microporous membranes of each of the culture chambers.

Continuous blood perfusion through the blood flow passageway may be provided by connecting the blood inlet means and the blood outlet means into an arterio-venous shunt constructed in a living donor animal. In this manner, the perfused blood serves as the nutrient source for the cells or tissues in culture, with continuous diffusion of plasma solutes and cell products taking place between the perfused blood and the cells or tissues through the microporous membrane which maintains the cells or tissues separated from the cellular components of the perfused blood. The system capable of supporting high density cell and tissue is growth, as well as being capable of long-term patency with respect to the perfused blood.

BRIEF DESCRIPTION OF THE DRAWINGS

Other features and advantages of the present invention will be apparent from the following detailed description of preferred embodiments accompanied by the attached drawings, in which:

FIG. 1 is a perspective view of a cell and tissue culture apparatus in accordance with the present invention and shown schematically as being connected into an arterio-venous shunt constructed in a living donor animal;

FIG. 2 is an enlarged sectional view of the cell and tissue culture apparatus taken along the line 2—2 of FIG. 1; and FIG. 3 is an enlarged fragmented sectional view of the cell and tissue culture apparatus taken along the line 3—3 of FIG. 1.

DESCRIPTION OF PREFERRED EMBODIMENTS

Referring now to FIG. 1 of the drawings, a cell and tissue culture apparatus 10 in accordance with the present invention is shown in its referred embodiment as comprising a rectangular housing formed of a central core assembly 12 disposed between identical top and bottom culture chamber assemblies 14 which are bonded to the upper and lower surfaces, respectively, of the central core assembly 12, as described more fully hereinafter. Each culture chamber assembly 14 has an outer wall member 16 provided with a plurality of cell and tissue introduction and retrieval ports 18 extending therethrough. The central core assembly 12 is provided at one end thereof with both a blood inlet conduit 20 leading into the housing, and a blood outlet conduit 22 leading out of the housing. As shown in FIG. 1, the cell and tissue culture apparatus 10 is connected into an arterio-venous shunt constructed in a living donor animal by having the blood inlet conduit 20 connected via tubing connector 24 to arterial tubing 26 leading from the animal's artery, and the blood outlet conduit 22 connected via tubing connector 28 to venous tubing 30 leading to the animal's vein.

Referring now to FIG. 2, the central core assembly 12 includes a rectangular frame member 32 formed of a suitable blood-compatible material, such as silicone rubber, and composed of a forward transverse wall 34 and a rearward transverse wall 36 joined together by a first outer longitudinal wall 38, a second outer longitudinal wall 40 and an intermediate longitudinal wall 42. The three longitudinal walls are equally spaced from each other so as to define two parallel longitudinally extending cavities of equal dimensions, the first cavity 44 being disposed between the intermediate longitudinal wall 42 and the first outer longitudinal wall 38, and the second cavity 46 being disposed between the intermediate longitudinal wall 42 and the second outer longitudinal wall 40.

The first and second cavities 44 and 46 are interconnected in series by means of a connecting conduit 48 joined to the exterior of the rearward transverse wall 36 of the frame member 32 and forming an integral part of the central core assembly 12. The connecting conduit 48 is formed of a suitable blood-compatible material, such as silicone rubber, and comprises a length of tubing closed at each end by means of plugs 50 and bonded along its length to the exterior of the rearward transverse wall 36 of the frame member 32 so as to extend longitudinally across the rearward ends of the two cavities 44 and 46 perpendicular to their lengths. Communication is provided between the connecting conduit 48 and the first cavity 44 by means of a series of flow ports 52 extending through the rearward transverse wall 36 of the frame member 32 and the contiguous wall of the conduit, and a similar series of flow port 54 provides communication between the connecting conduit 48 and the second cavity 46. In each of the two series of flow ports 52 and 54, the flow ports have a size gradient along the length of the connecting conduit decreasing in the direction of flow from the first cavity 44 to the second cavity 46 in order to equalize the flow through the flow ports.

The blood inlet conduit 20 and the blood outlet conduit 22 are conveniently constructed as a single length of tubing formed of a suitable blood-compatible material, such as silicone rubber, and bonded along its length to the exterior of the forward transverse wall 34 of the frame member 32 so as to form an integral part of the central core assembly 12. Separation of the blood inlet conduit portion of the tubing from the blood outlet conduit portion thereof is provided by means of a diverting plug 56 inserted in the tubing adjacent to the intermediate longitudinal wall 42 of the frame member 32, thereby serving to close the blood inlet conduit 20 at its downstream end and to close the blood outlet conduit 22 at its upstream end. The blood inlet conduit 20 thus extends longitudinally across the forward end of the first cavity 44 perpendicular to the length of the cavity, and the blood outlet conduit 22 likewise extends longitudinally across the forward end of the second cavity 46 perpendicular to the length of the cavity. Communication is provided between the blood inlet conduit 20 and the first cavity 44 by means of a series of flow ports 58 extending through the forward transverse wall 34 of the frame member 32 and the contiguous wall of the blood inlet conduit 20, and a similar series of flow ports 60 extending through the forward transverse wall 34 of the frame member 32 and the contiguous wall of the blood outlet conduit 22 provide communication between the blood outlet conduit 22 and the second cavity 46. In each series of flow ports 58 and 60, the flow ports have a size gradient along the length of the respective conduit decreasing in the direction of flow through the conduit in order to equalize the flow through the flow ports.

Referring now to FIG. 3, each of the two culture chamber assemblies 14 is formed by superimposing upon the inner surface of the respective outer wall members 16, a thin flexible blood-compatible microporous membrane 62, and bonding together the outer wall member and the microporous membrane around their peripheries. Such microporous membranes are known materials having holes of controlled shape and size running through their thickness and are commercially available in various pore sizes. For example, polycarbonate microporous membranes are commercially available under the trademark "NUCLEPORE" from the Nuclepore Corporation. For use in the cell and tissue culture apparatus of the present invention, the pore sizes of the microporous membranes should be such as to render the membrane permeable to plasma solutes and to cell products and impermeable to blood cellular components. Pore sizes effective for such purposes range broadly from about 0.015 to about 0.6 microns in diameter, and preferable from about 0.2 to about 0.4 microns in diameter.

In each of the two culture chamber assemblies 14, the space between the outer wall member 16 and the microporous membrane 62 constitutes a culture chamber 64. The outer wall members 16 are preferably formed of a clear, durable material such as polycarbonate to provide visibility of the cells or tissues being cultured within the culture chambers 64. The cell and tissue introduction and retrievall ports 18 extend through the outer wall members 16 and into communication with the culture chambers 64. The ports 18 are preferably formed of stainless steel tubing and are provided with removable cap members 66. The spacing between each outer wall member 16 and its respective microporous membrane 62 should be such that each culture chamber 64 in its empty condition is substantially flat, whereby the introduction of cells or tissues thereinto through the ports 18 results in the cells or tissues becoming wedged against the microporous membrane and thereby being maintained in close contact therewith so as to minimize molecular diffusion distances between the cells or tissues and the perfused blood across the microporous membrane.

To complete the assembly of the cell and tissue culture apparatus 10, the exposed surfaces of the microporous membranes 62 of the top and bottom culture chamber assemblies 14 are bonded, respectively, to the upper and lower surfaces of the central core assembly 12 along all their points of contact. In this manner, as best seen in FIG. 3, a blood flow passageway 68 is formed between the two microporous membranes 62 which are arranged within the housing in spaced parallel relation to each other, and the two culture chambers 64 are on opposite sides of the blood flow passageway 68 and in communication therewith only through their respective microporous membranes 62. As best seen in FIG. 2, the blood flow passageay 68 extends continuously from the blood inlet conduit 20 to the blood outlet conduit 22 through, in sequence, the series of flow ports 58, the first cavity 44, the series of flow ports 52, the connecting conduit 48, the series of flow ports 54, the second cavity 46, and the series of flow ports 60. The first cavity 44 and the second cavity 46 constitute sections of the blood flow passageway 68 which extend across separate parallel areas of the surface of each microporous membrane 62. Such design of the blood flow passageway 68 permits flow of perfused blood through the apparatus at a sufficiently high linear velocity so as to minimize significant thrombosis.

When utilizing the culture apparatus 10 for culturing biological cells and tissues, the apparatus should first be sterilized, then primed with heparinized saline, and thereafter connected into the arterio-venous shunt as illustrated in FIG. 1. A period of time sufficient to allow for the equilibration of the culture chamber contents with the plasma of the perfused blood, for example, about four hours, should precede cell or tissue implantation. Thereafter, the biological cells or tissues to be cultured are introduced into each of the two culture chambers 64 through their respective ports 18. Due to the substantially flat design of the culture chambers 64 in their empty condition, the introduction of the cells or tissues thereinto results in the cells or tissues becoming wedged against the respective microporous membrane 62 and thereby being maintained in close contact therewith. As the blood flowing in the arterio-venous shunt is continuously perfused through the blood flow passageway 68, the perfused blood simultaneously contacts the blood flow passageway surfaces of the microporous membranes 62 of each of the two culture chambers 64, whereby continuous diffusion of plasma solutes and cell products takes place between the perfused blood and the cells or tissues in each of the culture chambers 64 through the respective microporous membranes 62, which serve to maintain the cells or tissues separated from the cellular components of the perfused blood.

The close contact maintained between the cells or tissues and the microporous membranes minimizes molecular diffusion distances between the perfused blood and the cells or tissues. The blood flow passageway design permits the flow of the perfused blood through the system at a linear velocity sufficiently high so as to minimize significant thrombosis, thereby enabling the system to have long-term patency with respect to blood flow, i.e., for several days or weeks, and to support high density cell and tissue growth.

The tissue culture system in accordance with the present invention may include a plurality of culture apparatuses 10 connected together in series in an arterio-venous shunt constructed in a living donor animal, with the blood outlet conduit 22 of one culture apparatus 10 being connected to the blood inlet conduit 20 of an adjacent culture apparatus 10. In this way, large quantities of cells and tissues can be simultaneously cultured in a single culture system. Furthermore, if endocrine tissue, such as, for example, pancreatic islet tissue, parathyroid tissue, pituitary tissue or adrenal tissue, is placed in culture in the system of the present invention, the hormones released by the endocrine tissue would diffuse directly back into the perfused blood and, consequently, the system would act as a hybrid artificial endocrine system.

A cell and tissue culture apparatus designed as described above, and having approximate dimensions of four $\times$ six inches, was constructed employing one-eighth inch thick polycarbonate sheets as the outer wall members 16, and polycarbonate microporous membranes having an average pore diameter of 0.4 microns as the microporous membranes 62. Stainless steel tubing inserted through holes drilled in the polycarbonate sheets served as the cell and tissue introduction and retrieval ports 18. The frame member 32 was made of silicone rubber and was formed by injection molding on a heated, laboratory hydraulic press and postcured for sixteen hours at 180° C. Medical grade silicone rubber tubing, three-sixteenths inch I.D., five-sixteenths inch O.D., was employed for the blood inlet conduit 20, the blood outlet conduit 22 and the connecting conduit 48. The flow ports 52, 54, 58 and 60 were formed by using a cork borer to drill through the wall of the silicone rubber frame member and into the lumen of the silicone rubber tubing. Silicone rubber adhesive was injected into the tubing lumen at the appropriate places in order to form the conduit plugs 50 and 56. All bonded surfaces were primed with industrial grade silicone rubber adhesive primer, and bonding was accomplished with industrial grade silicone rubber adhesive. The total membrane surface area of the apparatus was 124 square centimeters. The arterial tubing 26 and the venous tubing 30 were medical grade silicone rubber tubing, three-sixteenths inch I.D., five-sixteenths inch O.D., and the tubing connectors 24 and 28 were silicone rubber coated, stainless steel tubing, one-fourth inch I.D., five-sixteenths inch O.D. The vascular circuit was completed by bonding 0.132 inch I.D. vascular catheters of spring reinforced polyurethane tubing to the free ends of the arterial tubing 26 and venous tubing 30, respectively.

Prior to connecting the blood inlet conduit 20 and the blood outlet conduit 22 of the culture apparatus constructed as above to the arterial tubing 26 and the venous tubing 30, an arterio-venous shunt was constructed in a Dorset lamb, by the following procedure. The lamb was anesthetized with halothane, and using sterile technique, the vascular catheters were advanced into the aorta via the subclavian artery and into the vena cava via the cephalic vein. At the time of cannulation, a loading dose of heparin was given (500 units/kg of body weight), together with penicillin, 200,000 units, and Streptomycin, 250 mg. The arterial and venous tubing were connected together, and shunt flow was established at approximately 400 ml/min, as measured by an in-line flow probe. The animal was transported to the tissue culture area where it was housed in an enclosed cage that was maintained at 31° C. The animal was fully awake throughout the duration of the procedure. The shunt tubing was placed in the tissue culture hood, where all manipulations were carried out. A continuous heparin infusion in isotonic saline was maintained at the rate of 75 units/kg of body weight/hour. Penicillin G was given intravenously in a dose of 250,000 units over two days along with the heparin infusion.

The tissue culture apparatus, after being gas sterilized in ethylene oxide for 12 hours, then degassed under vacuum for 48 hours, and thereafter primed with approximately 6 ml of 0.9% normal saline that contained 10 units/ml of sodium heparin, was then connected into the arterio-venous shunt by connecting its blood inlet conduit 20 to the arterial tubing 26, and its blood outlet conduit 22 to the venous tubing 30. All mainpulations were performing using strict sterile technique. After about 4 hours of blood perfusion through the culture apparatus, the contents of the culture chambers 64 had equilibrated with the plasma of the perfused blood.

Two separate experiments were carried out to determine the tissue culturing effectiveness of the cell and tissue culture system described above. In each experiment, prior to tissue innoculation, the chamber ports 18 were surface sterilized with 70% ethanol.

In the first experiment, the system was employed for culturing a rat soft tissue sarcoma that had been previously induced with methylcholanthrene and passaged in male Fischer rats. The tumor tissue was obtained under sterile conditions from a donor rat, and 300 mg thereof was sectioned into 1 to 2 mm cubes in a modified (1200 mg of $NaHCO_3$ added per liter to adjust pH to 7.4; 4000 units of sodium heparin added per liter) Earle's balanced salt solution at 4° C. The suspension of fragments was then aspirated into a syringe along with 1-2 cc of medium, and was injected forcefully into the culture chambers 64 of the culture apparatus 10 in order to distribute the tissue over the microporous membrane surface. The culture chamber ports were then sealed. Tissue culture was carried out for a period of 7 days, during which tissue growth was observed through a dissecting microscope. Black and white negatives and color slides were taken using a 35 mm camera mounted on a light microscope at 10×magnification. Incident light was used for illumination. At the termination of the experiment, the culture apparatus was removed from the shunt circuit, part of the harvested culture was re-suspended in modified Earle's salt solution and the remainder of the harvested culture was fixed in situ on the microporous membrane by injecting Bouin's solution into the culture chamber via the ports. Selected areas were processed for cross section, while others were prepared as whole mounts. H and E stains were used.

The results of the experiment showed that tissue fragments of the rat soft tissue sarcoma exhibited cellular proliferation within 24 to 48 hours of culture. The most pronounced change in the culture at this time was the formation of tissue bridges between implants. These bridges progressively enlarged throughout the duration of the culture period. Prior to bridge formation, there was no physical contact between the implants. The bridges were cellular in nature and composed of sarcoma cells. After 7 days in culture, the rat tumor had formed a nearly confluent new whitish tissue in many areas of the culture chamber, and the sarcoma cells were essentially spherical as they proliferated over the microporous membrane. This was similar to the shape of the cells in the actual tumor. In contrast, when the sarcoma cells were grown in standard polystyrene culture dishes, they assumed a more flattened form on the dish surface and never proliferated as a whitish tissue.

The rat soft tissue sarcoma cultured in the present culture system grew in layers 12 to 18 cells deep. The cells were closely packed, ranging in depth from 50 to 100 microns, and attained tissue-like densities. Assuming tissue specific gravity to be approximately 1, the sarcoma cell layer would have a mass of approximately 500-1000 mg per 100 $cm^2$ of membrane surface area.

The part of the harvested rat sarcoma culture that was re-suspended in modified Earle's salt solution, was used to test the viability of the cultured rat cells. Approximately $5 \times 10^5$ cells were injected subcutaneously into 6 male Fischer rats. Each of the 6 rats developed a rapidly growing tumor of the same histological type as the initially implanted tumor. This is comparable to the effectiveness (100% of 10 animals) of tumor induction observed when $5 \times 10^5$ native sarcoma cells were used as a control for the routine passage of the tumor between the Fischer rats.

In the second experiment, the system was used for culturing fetal sheep thymus. 115-Day gestation, fetal sheep thymus was obtained sterilely, and was sectioned, innoculated and cultured following the procedure described for the rat sarcoma, except that the culture period was for 9 days, and the viability test omitted. In situ observations of the originally implanted thymic tissue fragments revealed a slow, progressive decrease in size of the larger implants that was first noted after approximately 48 hours in culture. In contrast to this implant size decrease, on the fifth and sixth days of culture, many new, small spherical colonies of whitish tissue were noted to appear. These colonies, which were scattered throughout the culture, progressively enlarged until the cultures were harvested after 9 days of growth. Histologically, these were composed of cells resembling those of thymic epithelium. Cells remaining in the original implants were predominantly epithelial in appearance, with few lymphocytes identifiable.

The embodiments of the invention in which an exclusive property or privilege is claimed are defined as follows:

1. An apparatus for culturing biological cells and tissues employing perfused blood as the nutrient source, comprising:

(a) a housing means provided with a blood inlet means and a blood outlet means;
(b) a pair of culture chambers arranged within said housing means in spaced parallel relation to each other between two opposite walls of said housing means, each culture chamber being defined by a wall of said housing means and a thin flexible blood-compatible microporous memberane superimposed upon said wall and bonded thereto around its periphery, the spacing between said wall and said microporous membrane being such as to maintain said microporous membrane in close contact with cells or tissues introduced into said culture chamber, said microporous membrane being permeable to plasma solutes and to cell products and impermeable to blood cellular components;

(c) a blood flow passageway disposed within said housing means exterior of said culture chambers and extending continuously from said blood inlet means to said blood outlet means, said blood flow passageway including a plurality of sections, each of which extends across a separate parallel area of the surface of said microporous membrane so as to provide contact of said surface with blood perfused through said passageway, said culture chambers being arranged on opposite sides of said blood flow passageway, whereby blood perfused through said passageway simultaneously contacts the surfaces of the microporous membranes of each of said culture chambers;

(d) means in said walls of said housing means communicating with said culture chambers for introduction and retrieval of the cells and tissues; and (e) connector means for connecting adjacent sections of said blood flow passageway in series, said connector means comprising a conduit closed at each end and extending longitudinally across the ends of the two adjacent sections to be connected perpendicularly to the direction of blood flow through the sections, each of said two adjacent sections being provided with a series of flow ports communicating with said conduit along the length of the conduit, the flow ports in each of said series having a size gradient decreasing in the direction of blood flow through said conduit in order to equalize the blood flow through said flow ports;

said blood inlet means comprising an inlet conduit closed at its downstream end and extending longitudinally across the inlet end of said blood flow passageway, and said blood outlet means comprising an outlet conduit closed at its upstream end and extending longitudinally across the outlet end of said blood flow passageway, said inlet end and said outlet end of said blood flow passageway each being provided with a series of flow ports communicating respectively with said inlet conduit and said outlet conduit along the length of the respective conduit, the flow ports in each of said series having a size gradient decreasing in the direction of blood flow through the respective conduit in order to equalize the blood flow through said flow ports.

2. The apparatus of claim 1, wherein said blood inlet means and said blood outlet means are connected into an arterio-venous shunt constructed in a living donor animal, thereby providing continuous blood perfusion through said blood flow passageway.

* * * * *